US012745912B2

(12) United States Patent
Selvaraj et al.

(10) Patent No.: US 12,745,912 B2
(45) Date of Patent: Sep. 29, 2026

(54) DEVICE, SYSTEM, AND METHOD FOR DETERMINING PATIENT BODY TEMPERATURE

(71) Applicant: Vital Connect, Inc., San Jose, CA (US)

(72) Inventors: Nandakumar Selvaraj, San Jose, CA (US); Gabriel Nallathambi, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 321 days.

(21) Appl. No.: 16/378,728

(22) Filed: Apr. 9, 2019

(65) Prior Publication Data

US 2020/0323435 A1 Oct. 15, 2020

(51) Int. Cl.
*A61B 5/01* (2006.01)
*A61B 5/00* (2006.01)

(52) U.S. Cl.
CPC .............. *A61B 5/01* (2013.01); *A61B 5/0008* (2013.01); *A61B 5/6833* (2013.01); *A61B 5/7221* (2013.01); *A61B 5/725* (2013.01); *A61B 5/742* (2013.01); *A61B 2560/0223* (2013.01); *A61B 2560/0252* (2013.01)

(58) Field of Classification Search
CPC ....... A61B 5/01; A61B 5/0008; A61B 5/6833; A61B 5/725; A61B 5/742; A61B 5/7221; A61B 2560/0252; A61B 2560/0223
See application file for complete search history.

(56) References Cited

U.S. PATENT DOCUMENTS

| | | | | | |
|---|---|---|---|---|---|
| 5,735,604 | A * | 4/1998 | Ewals | G03G 15/2039 | 374/134 |
| 10,134,378 | B1 * | 11/2018 | Cenci | H03H 21/0012 | |
| 2009/0306536 | A1 * | 12/2009 | Ranganathan | A61B 5/6804 | 600/549 |
| 2010/0113894 | A1 * | 5/2010 | Padiy | G01K 13/20 | 600/301 |
| 2011/0158284 | A1 * | 6/2011 | Goto | A61B 5/01 | 374/163 |
| 2012/0029308 | A1 * | 2/2012 | Paquet | A61B 5/01 | 600/549 |
| 2013/0085708 | A1 * | 4/2013 | Sattler | G01K 1/20 | 702/131 |
| 2014/0288395 | A1 | 9/2014 | Leboeuf | | |
| 2017/0340208 | A1 | 11/2017 | Popovic | | |
| 2018/0049646 | A1 | 2/2018 | Ellis | | |
| 2018/0085070 | A1 * | 3/2018 | Chen | A61B 5/746 | |
| 2018/0160909 | A1 | 6/2018 | Damania et al. | | |
| 2018/0214028 | A1 | 8/2018 | Zhang | | |
| 2020/0397305 | A1 * | 12/2020 | Mensch | A61B 5/6832 | |

FOREIGN PATENT DOCUMENTS

| | | | | |
|---|---|---|---|---|
| CN | 108139274 A | | 6/2018 | |
| WO | WO-2013093485 A1 | * | 6/2013 | A61B 5/204 |

OTHER PUBLICATIONS

International Search Report and Written Opinion from International Application No. PCT/US20/26839 mailed Aug. 12, 2020, 13 pages.

* cited by examiner

*Primary Examiner* — Andrey Shostak
(74) *Attorney, Agent, or Firm* — Shih IP Law Group, PLLC.

(57) ABSTRACT

A wireless wearable sensor device, method, and non-transitory computer readable medium for determining patient body temperature based on a skin temperature and sensor ambient air temperature is disclosed.

15 Claims, 6 Drawing Sheets

300

DEVICE, SYSTEM, AND METHOD FOR DETERMINING PATIENT BODY TEMPERATURE

FIELD OF THE INVENTION

The present application relates to a device, system, and method for determining patient body temperature based on a wearable sensor measuring a first temperature at a body skin surface and a second temperature from sensor ambient air.

BACKGROUND

Core temperature is the temperature measured at the deep tissues of the body such as abdominal, thoracic and cranial cavities. Core temperature is endothermic regulated by the hypothalamus of the brain. The Gold Standard for measuring core temperature is pulmonary arterial or esophageal catheter. However, oral thermometer is commonly adapted in clinical settings to measure patient body temperature and requires correct placement in a sublingual pocket while keeping the mouth closed. Shortcomings to oral temperature measurement is that oral temperature measurement is an approximation to the core temperature and measures the temperature at an oral site that may be influenced by other external factors including drinking hot/cold beverages, eating and smoking for example. Axillary location, commonly known as an armpit which is another popular choice particularly for pediatric patients, has a relatively lower temperature than the patient's core body. Furthermore, axillary temperature measurement is not reliable due to its sensitivity to correct placement of the tip under arm, proper closing of arm alongside the body during the temperature measurement and presence of sweat and hair, in case of adults. Meanwhile, rectal temperature is the least popular choice due to inconvenience and compliance and has a relatively higher temperature than core-body. In all of the above direct mode patient temperature measurement choices, the output temperature is unadjusted direct temperature measurement from the measuring site to which a single thermometer or sensor probe is coupled. The traditional patient temperature measurement methods offer unique limitations related to inherent location dependent variability, environmental influences and convenience/practical aspects and not suitable for continuous uninterrupted patient monitoring. Therefore, novel low-power wireless wearable sensors can mitigate the above issues and provide continuous temperature measurements conveniently without interrupting the patient or user.

In one case, a single temperature sensor such as a thermistor embedded into a wearable sensor applied on a patient's skin surface anywhere on the body can provide measurement of local skin temperature (SkinTemp) either by direct unadjusted transformation of measured resistance to a temperature per the thermistor coefficient of resistance characteristics or with additional algorithmic adjustments accounting for the sensor's thermal properties. SkinTemp measurement at a body surface using a single thermistor is ectothermic i.e., vastly influenced by local blood perfusion and external environment. Thus, SkinTemp may show high fluctuations influenced by external factors such as clothing covering the measurement site and the ambient changes in user's environmental surroundings. As a result, SkinTemp of a wearable sensor may be less useful for clinical patient monitoring and patient interventions in hospitals. Such limitations of SkinTemp and traditional patient measurement methods necessitates the need for a wearable sensor capable of measuring accurate patient body temperature continuously without the manual measurement errors and environmental influences. Therefore, there is a strong need for a solution that overcomes the aforementioned issues. The present application addresses such a need, and presents a wearable sensor measuring sensor ambient air temperature in addition to measuring SkinTemp and an algorithm to adjust the SkinTemp by cancelling the influence of sensor ambient air temperature (AmbTemp) to produce body temperature (is referred to as BodyTemp hereafter) that is comparable to the standard patient temperature.

SUMMARY

A method to determine patient body temperature is disclosed. In an embodiment, the method includes measuring, by a first sensor, a first temperature value at a skin surface on a patient body; measuring, by a second sensor, a second temperature value of the sensor ambient air temperature at or proximity to the first sensor; determining a thermal exchange at the skin surface on the patient body; determining the patient body temperature by using the first temperature value, the second temperature value, and the thermal exchange; and outputting a patient body temperature.

A wireless wearable sensor device for temperature monitoring is disclosed. In an embodiment, the wireless wearable sensor device includes a first sensor that measures a first temperature value at a skin surface on a patient body; a second sensor that measures a second temperature value of the sensor ambient air temperature at or proximity to the first sensor; a computing device including a memory and a processor, wherein the computer device receives the first and second temperature values and implements by the processor an application stored in the memory to determine a patient body temperature; and a display device that displays the patient body temperature.

A non-transitory computer-readable medium storing executable instructions that, in response to execution, cause a computing device of a wireless wearable sensor device to perform operations is disclosed. In an embodiment, the non-transitory computer-readable medium storing executable instructions that, in response to execution, cause a computing device of a wireless wearable sensor device to perform operations including measuring, by a first sensor, a first temperature value at a skin surface on a patient body; measuring, by a second sensor, a second temperature value of the sensor ambient air temperature at the first sensor; determining a thermal exchange at the skin surface on the patient body; determining the patient body temperature by using the first temperature value, the second temperature value, and the thermal exchange; and outputting a patient body temperature.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present application.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques to those skilled in the art may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with or in combination with other embodiments whether or not explicitly described.

The patient body temperature prediction stems from the physiology of human thermoregulation mechanism that balances internal metabolic heat production against external heat loss from the body surface through blood perfusion, radiation, conduction and convection processes. The human thermoregulation system attempts to cancel out fluctuations in atmospheric changes for normal operating environmental conditions such as ambient or environmental temperatures between 61° F. and 104° F. and maintains the internal core temperature to be constant. Thus, the relationship between the changes in environmental temperature versus core temperature or patient body temperature may remain constant for a normal range of environmental condition.

The above physiological relationship can be framed into a mathematical model as given below.

$$qc(T_b-T_s)=hA(T_s-T_a) \quad (1)$$

where, $T_b$ is the BodyTemp; $T_s$ is the SkinTemp; $T_a$ is the AmbTemp; q is the blood flow rate; c is the specific heat of the blood; his the heat transfer coefficient; A is the body surface area. Simplifying the above equation (1), $$T_b \propto \frac{hA}{qc}(T_s - T_a) \quad (2)$$

Based on the above theoretical framework, the BodyTemp prediction algorithm allows cancelling out the ambient variability from SkinTemp using accurate independent sampling of temperatures at two different interfaces of skin surface and sensor ambient air, estimating heat transfer or thermal exchange from core body to chest skin surface, and shifting the temperature output scale to be of similar scale to that of core temperature for comparisons.

Figure 1:
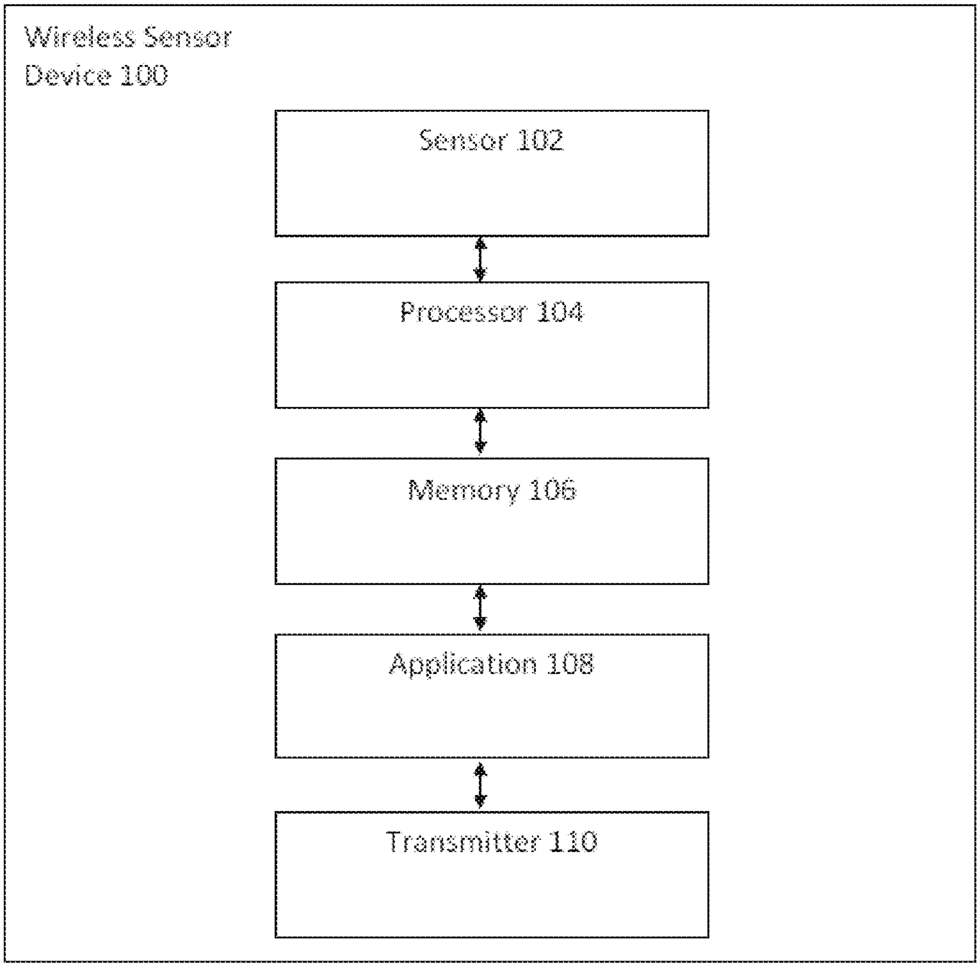
FIG. 1 illustrates a wireless wearable sensor device for health monitoring in accordance with an embodiment.

FIG. 1 illustrates a wireless wearable sensor device 100 for measuring a first temperature at a body skin surface and a second temperature from sensor ambient air. The wireless wearable sensor device 100 or wearable device includes a sensor(s) 102, a processor 104 coupled to the sensor(s) 102, a memory 106 coupled to the processor 104, a wireless wearable sensor device application 108 coupled to the memory 106, and a transmitter 110 coupled to the wireless wearable sensor device application 108.

The wireless wearable sensor device 100 is attached to a user to measure a first temperature at a body skin surface and a second temperature from the sensor ambient air. The sensor(s) 102 includes, but is not limited to, thermistor(s), respectively. The sensor(s) 102 obtains temperature data from the body skin surface and sensor ambient air around the sensor which is transmitted to the memory 106 and in turn to the wireless wearable sensor device application 108 via the processor 104. The memory 106 may be a flash memory. The processor 104 executes the wireless wearable sensor device application 108 to process and obtain information regarding the user's health. The information may be sent to the transmitter 110 and transmitted to another user or device for further processing, analysis, and storage. That is, the transmitter 110 may transmit the various temperature data to a remote device/server (e.g. smartphone, cloud-based server) for processing, analysis, and storage. The transmitter 110 may be a Bluetooth Low Energy (BLE) transceiver. Alternatively, the wireless wearable sensor device 100 may process and analyze the temperature data locally via the wireless wearable sensor device application 108 stored in memory 106 and implemented by the processor 104.

The sensor(s) 102 may be one or more thermistors, and the processor 104 is any of a microprocessor and a reusable electronic module. One of ordinary skill in the art readily recognizes that a variety of devices can be utilized for the sensor(s) 102, the processor 104, the memory 106, the wireless wearable sensor device application 108, and the transmitter 110 and that would be within the spirit and scope of the present application.

The wireless wearable sensor device 100 may be an ultra-low cost and fully disposable battery-operated adhesive biometric patch biosensor with integrated sensors/thermistors and a Bluetooth Low Energy (BLE) transceiver that is attached to the user's skin and used in conjunction with the electronic module to detect, record, and analyze a plurality of temperature data from the body skin surface and sensor ambient air around the sensor. The wireless wearable sensor device 100 continuously gathers temperature data from the patch wearer. The wireless wearable sensor device 100 may then encrypt and transmit the encrypted data via bi-directional communication to a Hub Relay, which in turn transfers the data to a Secure Server where it is stored for viewing, downloading, and analysis. With this information, the healthcare provider can observe improvement or degradation of patient's body temperature on a real-time basis and intervene if necessary. To improve delivery of biosensor events, events—including live events—are saved to flash memory on the wireless wearable sensor device 100 to avoid data loss. By storing data locally, the wireless wearable sensor device 100 does not need to maintain a constant Bluetooth connection. No data is lost when the wearer is out of Bluetooth range for example and reconnection occurs automatically when the wireless wearable sensor device 100 is within range of the Hub Relay. When the wireless wearable sensor device 100 has a connection to the relay, the wireless wearable sensor device 100 transmits data at regular intervals, and receives confirmation from the relay of successful transmission. The wireless wearable sensor device 100 may include onboard flash memory that stores firmware, configuration files, and sensor data. The health-care provider can configure how the sensor collects data. Individual data streams (such as temperature data) may be enabled or disabled, depending on how the biosensor will be used.

The temperature data from the body skin surface and sensor ambient air around the sensor are then processed and analyzed using either integrated processors and algorithms of the wearable device 100 (e.g. the reusable electronic module or system-on-chip board) or an external processing device (e.g. smartphone device, cloud-based server network).

Additionally, one of ordinary skill in the art readily recognizes that a variety of wireless wearable sensor devices can be utilized including but not limited to wearable devices, that would be within the spirit and scope of the present application.

Figure 2:
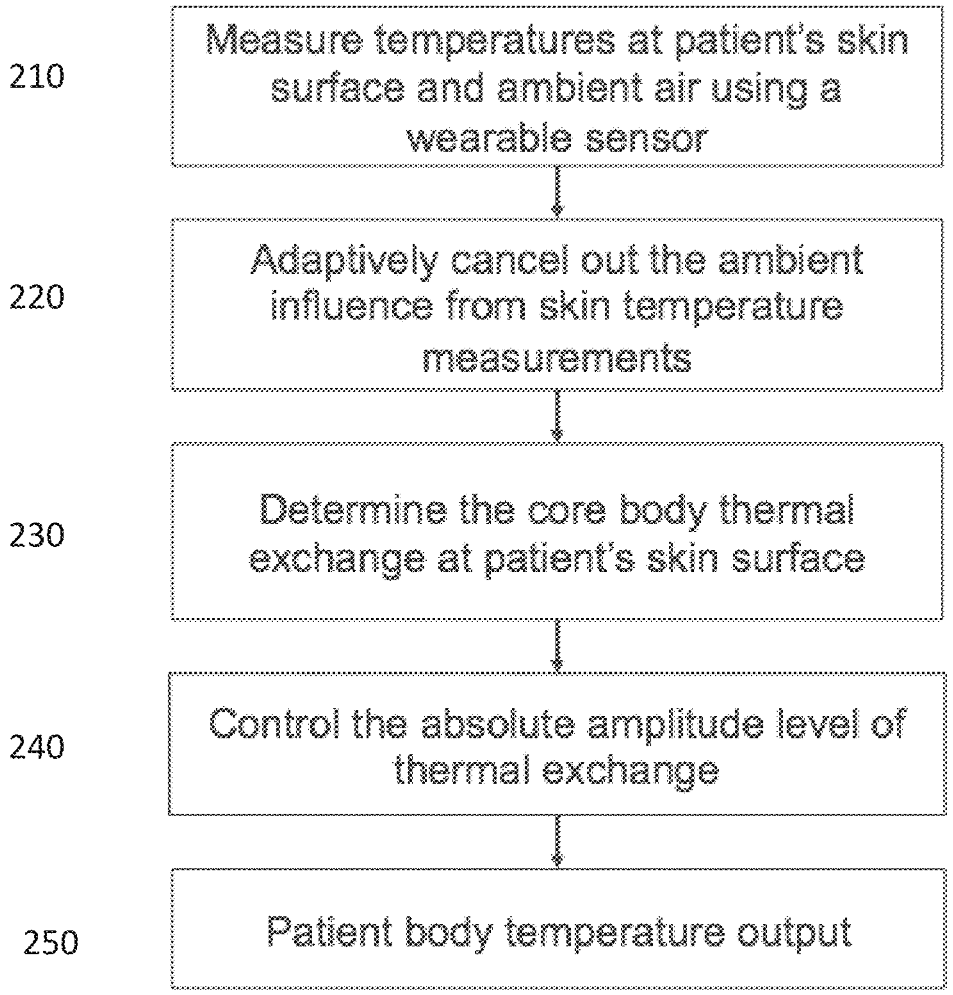
FIG. 2 illustrates a flow chart for determining patient body temperature.

FIG. 2 illustrates a flow chart 200 for determining patient body temperature (denoted as BodyTemp here forth). Accordingly, a wearable sensor is used to measure two or more temperature values at patient's skin surface on the body and sensor ambient air surrounding the sensor at 210. The ambient temperature fluctuations are adaptively cancelled from the skin temperature measurements by using, for example, an adaptive filter at 220. The core body thermal exchange, also described as a heat flux, a heat transfer, or a core body thermal transfer, at patient's body surface is determined by subtracting the ambient filter output from skin temperature values 230. The absolute amplitude values of the derived core body thermal exchange is controlled and modified by subtracting the thermal exchange DC offset and adding a calibration input value that transforms the time varying quantity of the core body thermal exchange at 240. The scale shifted thermal exchange is output as the patient body temperature at 250. Additional details of the above system and method for patient body temperature measurement is described by a flow chart representation in FIG. 3.

Figure 3:
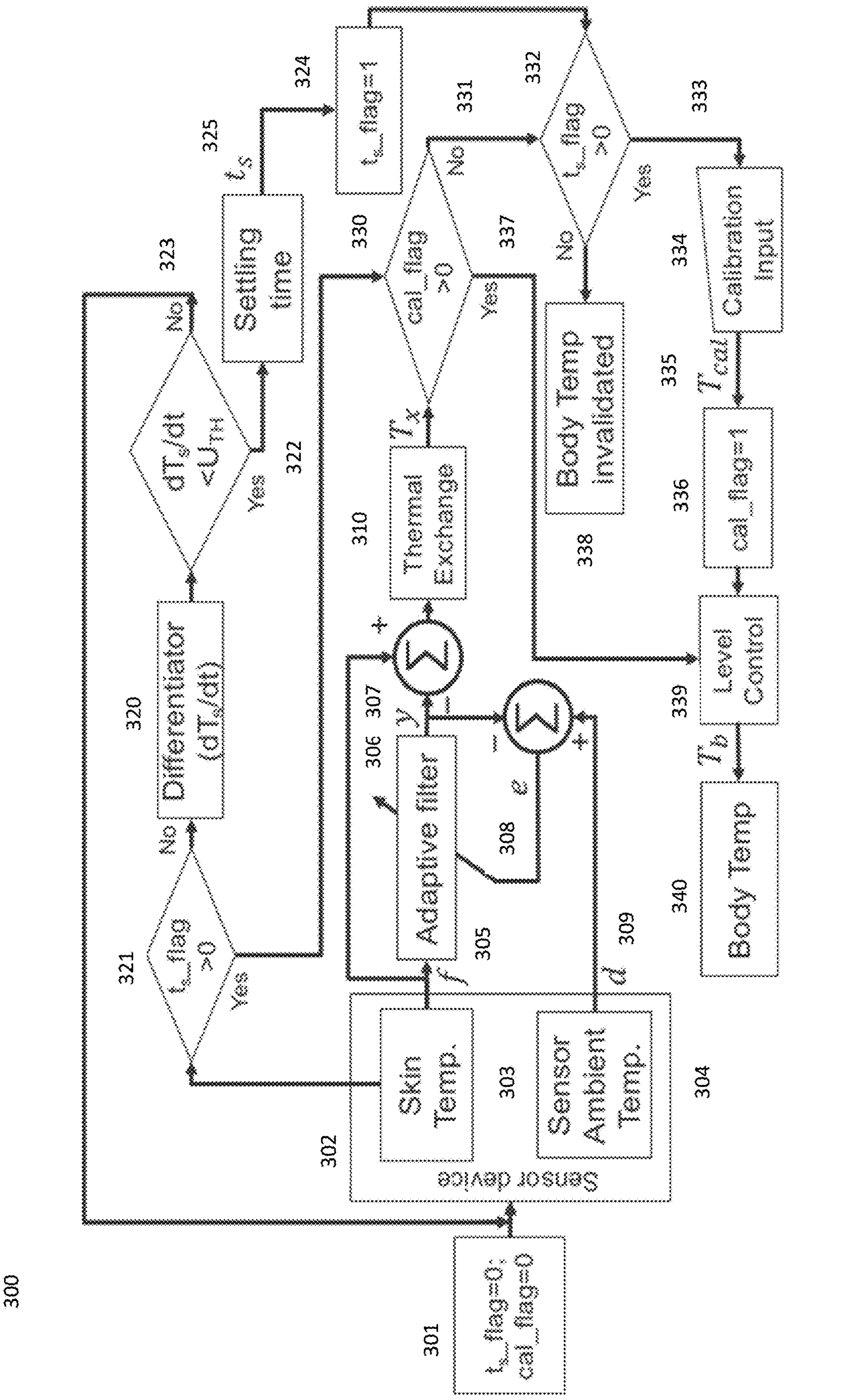
FIG. 3 illustrates a flow chart of the patient body temperature prediction algorithm.

FIG. 3 illustrates a flow chart 300 of the patient body temperature prediction algorithm. The patient body temperature assessment starts with initialization of settling time flag ($t_s$_flag) and a calibration flag (cal_flag) with initial values of zero at 301. A wearable sensor device 302 may include two or more temperature transducers that allow independent direct sampling of temperatures at skin body surface 303 (denoted as SkinTemp here forth) and sensor ambient air 304 in proximity (denoted as AmbTemp here forth). If more than one transducer network is used for measurement of SkinTemp, an appropriate statistical measure including average or median is calculated from the outputs of the temperature transducer network to refer as SkinTemp. Similarly, one or more independent temperature transducer network may be employed to determine the AmbTemp measurement. Moreover, the temperature transducer used to measure SkinTemp and AmbTemp may have different resolution and sampling frequencies, in which case both the measurements may be converted to the same value of higher or lower resolution and sampling frequency respectively depending on performance specifications. The temperature transducer such as thermistors, resistance thermometer detectors (RTD) and thermocouple, a wearable sensor device such as adhesive patch sensor, pendant, wrist-band, wrist-watch or an electronic module adhered to body are within the scope of this application. Thus, the wearable sensor system may allow independent direct sampling of SkinTemp from skin surface and AmbTemp from sensor ambient air using two or more temperature transducer network.

The input values of SkinTemp {f(n)} 305 is passed through an adaptive filter 306 to produce an output sequence {y(n)} 307, i.e. an adaptive filter output. The filter coefficients are updated by minimizing the error 308, $$e(n)=d(n)-y(n) \tag{3}$$

where, {d(n)} 309 is the desired reference input values of AmbTemp.

The adaptive filter output is subtracted from the input SkinTemp to determine the thermal exchange between skin surface and the core body 310 as $$T_x(n)=f(n)-y(n) \tag{4}$$

that quantify the time varying change in thermal exchange between the core body and skin surface.

At the same time, the SkinTemp {f(n)} is passed through a differentiator 320 that may determine the difference between current and previous SkinTemp values over a unit time difference (i.e., $$\frac{dT_s}{dt}$$

where, $T_s$ is the SkinTemp) only if the ts_flag 321 is not currently onset (i.e., ts_flag=0). The calculated derivative of SkinTemp $$\frac{dT_s}{dt}$$

is compared to a threshold of $U_{TH}$ (for example, 0.01 which is 10% of SkinTemp unit display resolution for example of 0.1 (that corresponds to a 90% reduction of rate of change in SkinTemp due to settling process). In another example, the SkinTemp derivative is filtered or averaged over a predetermined time window to be compared to a threshold such as 5% or other values of unit display resolution. If $$\frac{dT_s}{dt}$$

is found to be $<U_{TH}$ at 322 then the time elapsed until then to satisfy this condition will be determined as the settling time $t_s$ 325 of the temperature sensor(s). On the other hand, if $$\frac{dT_s}{dt}$$

is not less than $U_{TH}$ at 323, the upcoming samples of SkinTemp will be passed through the differentiator 320, comparing to determine whether the condition $$\frac{dT_s}{dt} < U_{TH}$$

is satisfied until the settling time is reached. Once the settling time is reached by satisfying the above condition and $t_s$ is determined for the continuous measurement, then the ts_flag will be set to be 1 at 324 (i.e., ts_flag=1). After the onset of ts_flag, the processing with the differentiator 320 and comparing the above condition will be ceased.

After the simultaneous and continuous determination of whether the settling time flag is onset or not and an estimate of heat flux as a measure of local thermal exchange, the algorithm now determines whether the calibration flag (i.e., cal_flag) is already set or not by checking the current value of cal_flag whether it is 0 or >0 at 330. If the cal_flag is not >0 at 331 (i.e, cal_flag value is still 0), then algorithm checks the settling time flag onset at 332 (ts_flag>0?). If the cal_flag is not onset and the ts_flag is already set at 333 (ts_flag>0), a calibration value $T_{cal}$ 335 will be prompted to obtain from a reference device and input to the algorithm via an appropriate user interface at 334. Once the calibration input $T_{cal}$ is received, the cal_flag will be onset to 1 at 336 (i.e., cal_flag=1) and the algorithm would not require any further calibration input values for continuous determination of patient BodyTemp 340. Despite that, if the user prompts to feed in calibration input (recalibration) via the user interface, the algorithm would consider the latest user input for calculation of patient BodyTemp 340. On the other hand, if the calibration flag is not onset and the settling time flag is also not onset at 337, the BodyTemp output from the algorithm will be invalidated at 338 until both the settling time and calibration input are completed. The invalidation code of an invalid BodyTemp output can be a unique numerical value such as a negative numerical value or positive greater numerical value outside the human temperature range. In one case, if the calibration input is obtained immediately after the biosensor application, the BodyTemp value can be simply output as the input calibration value until the temperature sensors are still settled down to a steady state.

After a settling time of $t_s$ and receiving a calibration input $T_{cal}$, the absolute value of core body thermal exchange will be determined as the settling offset $T_{so}$ at the block of level control 339, and the patient body temperature outputs are calculated with the following equation, $$T_{so}=T_x(n), n=t_s*f_s \qquad (5)$$

$$T_b(n)=T_x(n)-T_{so}+T_{cal}, n\geq t_s*f_s \qquad (6)$$

where, $T_b$ is the body temperature output; $T_{so}$ is the settling offset temperature; $t_s$ is the settling time of the sensor; $f_s$, is the sample rate of f, SkinTemp; $T_{cal}$, is the patient temperature input from a reference device. The absolute levels of the BodyTemp output 340 is controlled by the user's calibration input 334. Without the level control 339 input such as calibration value, the relative change in thermal exchange, $T_x$ may not have an absolute scale comparable to that of standard temperature measurement range. In such case, the trend in relative changes of thermal exchange, $T_x$ can be used to determine how much an increasing or decreasing change in the temperature the patient or user is experiencing from time-to-time rather than tying that change in temperature to an absolute scale that can distinguish normal or abnormal range. With the first calibration input $T_{cal}$, the thermal exchange $T_x$ is subtracted from its AC offset value $T_{so}$ and the input calibration value of $T_{cal}$ is added as DC in determining BodyTemp output with an absolute scale set by the calibration input. The patient BodyTemp output $T_b$ can be displayed by communicating to an appropriate display device such as a monitor, display, tablet, screen, etc., or transmitted for storage on a local sensor memory or a relay memory or a cloud. In one example, the construction of the wearable device 302 is modelled for example, as an FIR filter and applied to the temperature data from the body skin surface and sensor ambient air around the sensor to provide relatively more accurate adjusted temperature data sampled from the sensor 303 of body skin surface interface and the sensor 304 of ambient air interface in the wearable device. Then the corrected measurements of skin and ambient temperatures are used to determine the patient body temperature in method 300.

The adaptive filter 306 for determining patient BodyTemp 340 may be a set of instructions or a program defined by the filter type such as linear (including least mean square (LMS), recursive least squares (RLS) filters and their variants) or nonlinear (including Volterra and bilinear filters) or nonclassical (including artificial neural networks, fuzzy logic and genetic algorithms), structure (including transversal, symmetric, lattice and systolic array), parameters (including zeros, poles and polynomial coefficients) and adaptive algorithm (including stochastic gradient approach and least squares estimation) executed on a microprocessor or a digital signal processing chip or a field-programmable gate array or a custom very large scale integrated (VLSI) circuit, or a system-on-chip (SOC).

RLS Adaptive Filter

For example, consider a recursive-least-squares (RLS) adaptive filter with finite impulse response (FIR) coefficients of length M such as $b_k$ (k=0, 1, 2, . . . M−1) for the adaptive filter block 306 of patient BodyTemp prediction algorithm. The RLS filter can adapt effectively to time-varying characteristics of input temperature changes and converge quickly. In one example, the RLS filter implementation for adaptive cancellation of sensor ambient air from the SkinTemp is given below.

For the given new SkinTemp input vector f(n) 305 and the desired reference AmbTemp vector d(n) 309, compute the FIR filter output y(n) 307 using the previous set of filter coefficients b(n−1) as, $$y(n)=f^T(n)b(n-1) \qquad (7)$$

where, initialization of filter coefficients is as b(0)=0.

Compute the error as in equation (3).

Compute the Kalman gain vector as $$k(n) = \frac{R^{-1}(n-1)f(n)}{\lambda + f^T(n)R^{-1}(n-1)f(n)} \qquad (8)$$

where, λ is the system memory or the forgetting factor that affects the convergence and stability of the filter coefficients and ability of the filter to track time varying characteristics of input vector; R(n) is the autocorrelation matrix given as, $$R(n) = \sum_{i=0}^{n} \lambda^{n-i} f(i) f^T(i) \qquad (9)$$

where, the initialization of $R^{-1}(0)=\delta I$; δ, regularization parameter such as 0.01; I, is the identity matrix.

Update the inverse correlation matrix $R^{-1}(n)$ for the next iteration as, $$R^{-1}(n)=\lambda^{-1}[R^{-1}(n-1)-k(n)f^{T}(n)R^{-1}(n-1)] \quad (10)$$

Update the filter coefficients for the next iteration as, $$b(n)=b(n-1)+k(n)e(n) \quad (11)$$

The parameters of the RLS filter, for example, can be chosen as follows: order of the filter M as 1, the forgetting factor λ as 0.9999, and the regularization factor δ as 0.1.

In cases of system power reset and reapplication of wearable device on the user body, the adaptive filter parameters including filter coefficients b, error signal e, inverse correlation matrix $R^{-1}$, settling time flag ts_flag, calibration flag cal_flag are initialized to be zeros, and the above processes repeat to provide continuous BodyTemp output. In case of regular biosensor operation and a recalibration request that is when the user prompts to push new calibration value to the system via user interface, the BodyTemp algorithm retains the adaptive filter parameters for the adaptive determination of thermal exchange and shift the absolute scale of thermal exchange to a new DC level according to the new calibration (i.e., recalibration) input value. The proposed algorithm and system allow multiple recalibrations as required by the user/health care provider/clinical administrator. However, in case of frequent recalibrations, the trend in BodyTemp output needs to be interpreted taking the multiple recalibration timings and input values into consideration.

Sample Settling Time Data

Figure 4B:
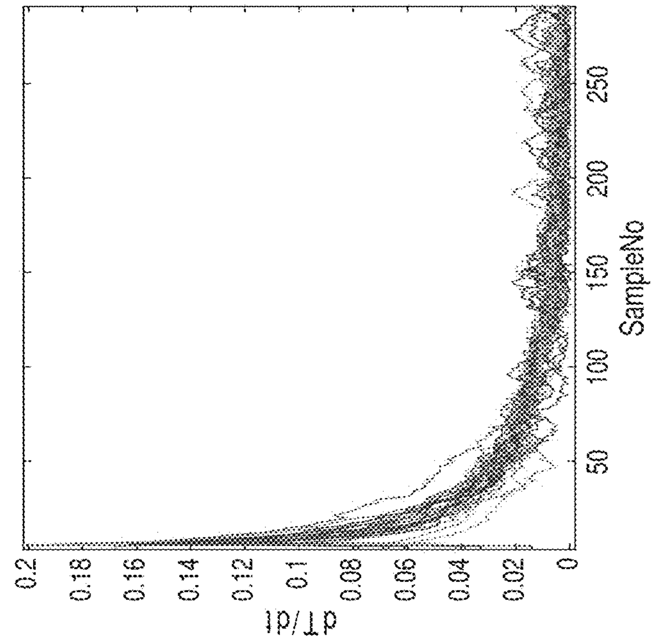
FIG. 4*b* illustrates a graph depicting the differences in successive SkinTemp values as their rate of change.
Figure 4A:
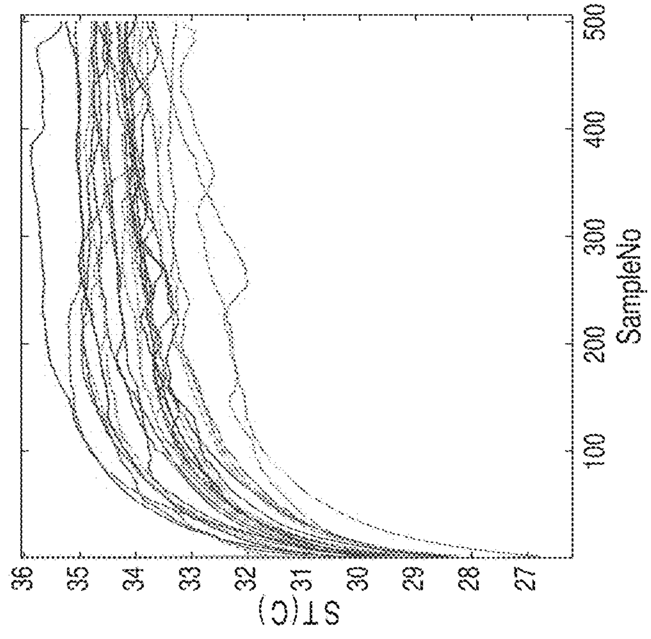
FIG. 4*a* illustrates a graph depicting SkinTemp time profiles recorded from a group of participants immediately after the adhesive sensor application.

Settling time of raw temperature data from the wearable sensor device applied on the patient may vary widely depending on the initial electrical response of the temperature transducer, patient's skin type, contact pressure or adherence of the sensor on the body surface. During the settling time the application of wearable sensor device on the skin surface, the measured raw temperature data from skin surface and sensor ambient air may show drastic change in their absolute values of the order of few to 10° C. range. Applying a calibration value to shift the derived BodyTemp scale before the raw temperature measurements settle down can lead to erroneous absolute scale throughout the sensor life, unless another recalibration is applied after settling time. Therefore, to minimize errors, the calibration input is applied to shift the absolute scale of derived BodyTemp after a settling time of good confidence. Thus, the settling time of the sensor assessed objectively using the raw temperature values per method 300 or predetermined based on the clinical data is utilized for accurate BodyTemp absolute measurement values. FIG. 4*a* shows tracings of temperature values measured at the chest skin surface after application. In another example, the calibration input can be obtained during the time of sensor application on the patient's body and be applied after the customized objective assessment of the settling time of the temperature transducer response for the BodyTemp prediction. This approach may be practical from the in-hospital work flow or other use cases standpoint by the observation that the patient temperature may not change drastically in few minutes. When the user/patient is normal during the sensor application and calibration, the rate of change of body temperature is a very slow frequency phenomenon over 24 hour cycle. However, if the user/patient is determined to be having a fever during sensor application and calibration, recalibration after a typical settling period or the patient temperature reaching a steady state is recommended or useful to obtain more accurate absolute BodyTemp values. Further, FIG. 4*a* depicts SkinTemp time profiles recorded from a group of participants immediately after the adhesive sensor application and FIG. 4*b* depicts the differences in successive SkinTemp values as their rate of change that show the inherent transient phase of settling process of temperature sensor outputs.

In one example, the settling time of temperature sensor can also be preset to a desired settling time duration, for example 30 min, based on the analysis of temperatures profiles obtained from a sample population. In this case, the automated determination of temperature sensor settling is replaced with a timer and checking if the timer is elapsed with the desired input settling time.

In another example of objective determination of whether the temperature sensor is settled after its warm up transient phase involves fitting a linear regression line (L=α×d+β, where α, is the slope of the line L and β, is the intercept or bias) with a predetermined moving time window (example, 5 min) of SkinTemp derivative samples and determining α, the rate of settling as the slope of the linear fit. The above process is repeated for every predetermined duration such as 1 min and the trend in a are tracked. The determined trend in α is further used to determine the settling period as the time when a reaches closes to zero with some tolerance (example 5% or 10%) or reaches a global minimum value over a certain start-up period.

Sample Predicted BodyTemp Data

Figure 5B:
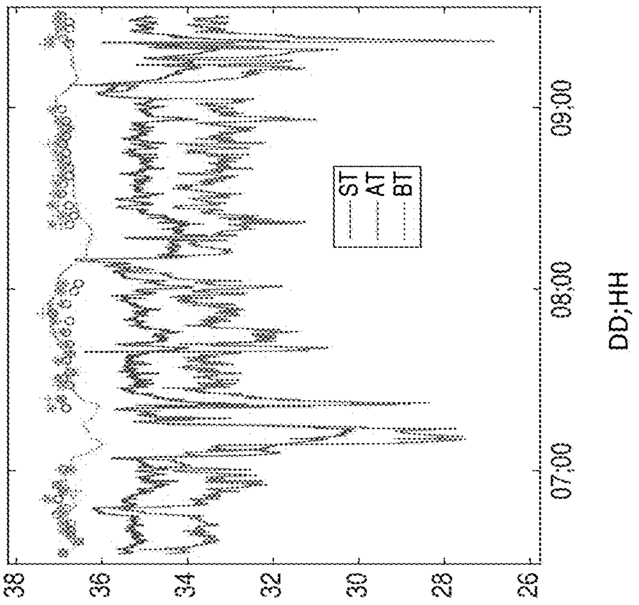
FIG. 5*b* illustrates a graph depicting BodyTemp output plotted together with SkinTemp, AmbTemp, and reference oral thermometer temperature (OralTemp) from the same sample record for comparison.
Figure 5A:
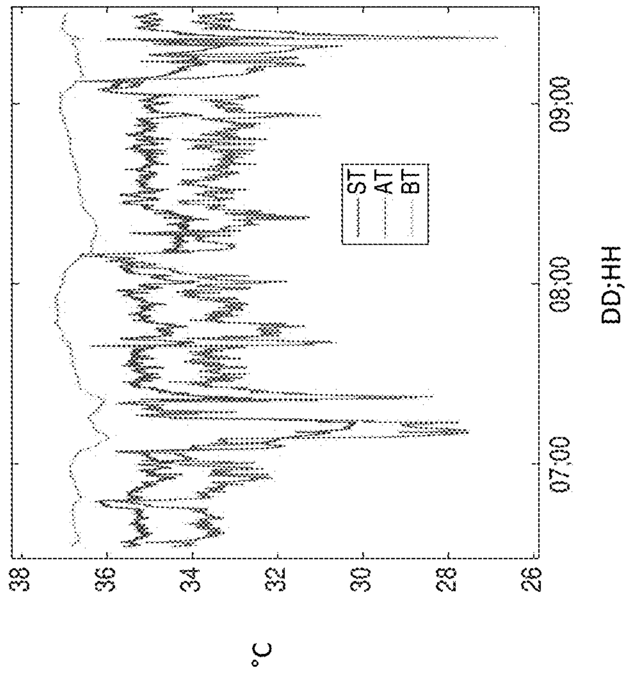
FIG. 5*a* illustrates a graph depicting BodyTemp output plotted together with SkinTemp and AmbTemp from the same sample record for comparison.

A sample SkinTemp (denoted with a legend ST) and AmbTemp (denoted with a legend AT) data collected over 3-days is shown in FIG. 5*a*. The plot shows high fluctuations of 2 to 6° C. in SkinTemp particularly during transitions from night to day times. Such high fluctuations in SkinTemp are not reflective of the 1° C. change typically observed in patient's core temperature during normal circadian cycles. Hence, the absolute measurements of SkinTemp may not be accurate in its direct form without any additional transformations or adjustments. The AmbTemp also shows similar fluctuations and predominantly influence these high fluctuations in SkinTemp. Thus, the BodyTemp algorithm adaptively cancels out the AmbTemp influence from SkinTemp to determine the BodyTemp. The BodyTemp output is plotted together with SkinTemp and AmbTemp from the same sample record for comparison in FIG. 5*a*. The predicted BodyTemp show a very stable trend with fluctuations of <1° C. in 3-day duration. FIG. 5*b* now includes OralTemp reference values (3 repeats) taken during the 3-day data collection in this control subject. There is a good correspondence between the reference OralTemp and predicted BodyTemp values.

Calibration Input

BodyTemp algorithm determines $T_x$, the time varying thermal exchange per equation (4), which is a continuous measure of the change of thermal exchange between the body and its surroundings. Further subtracting $T_{so}$ from $T_x$ after patch settling time can essentially remove the DC component of thermal exchange and provide only the AC component or delta change in thermal exchange. Thus, $(T_x-T_{so})$ refers to the pure AC component of the thermal exchange from the upper body that itself can be very useful for clinical monitoring of patient deterioration with infections or fever. However, this quantity may not have a similar absolute magnitude (scale) to that of a patient temperature with a DC value around 37° C. for example of a normal condition. In order to shift the scale of this AC thermal exchange similar to a clinical patient temperature, the quantity $(T_x-T_{so})$ is added to a DC component $T_{cal}$, a calibration input as given in equation (6) results in prediction of BodyTemp output $T_b$. Thus, a calibration temperature $T_{cal}$ shifts the scale of AC component of thermal exchange to a BodyTemp with a scale similar to that of the patient's temperature.

The calibration temperature $T_{cal}$ can be input to the BodyTemp algorithm via an appropriate user interface (UI) implemented on a computer, smart phone/device, tablet, etc. For example, the nurse or clinician can measure the patient temperature using a standard tool such as oral thermometer or another clinical patient temperature monitor, and manually input via the UI. BodyTemp prediction algorithm can be modified where the calibration input can be replaced by a transformation model trained by a large in-hospital clinical study for a wide range of patient temperature ranges from fever, infections and sepsis conditions with gold standard reference patient temperature measurement via an invasive thermistor probe. Further, the BodyTemp output can be modified to account for systemic bias adjustments compared to gold standard temperature reference measurements. In another example, transformations on learned SkinTemp error distributions may also be used as a surrogate for calibration input.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Furthermore, the present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and even apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Figure 6:
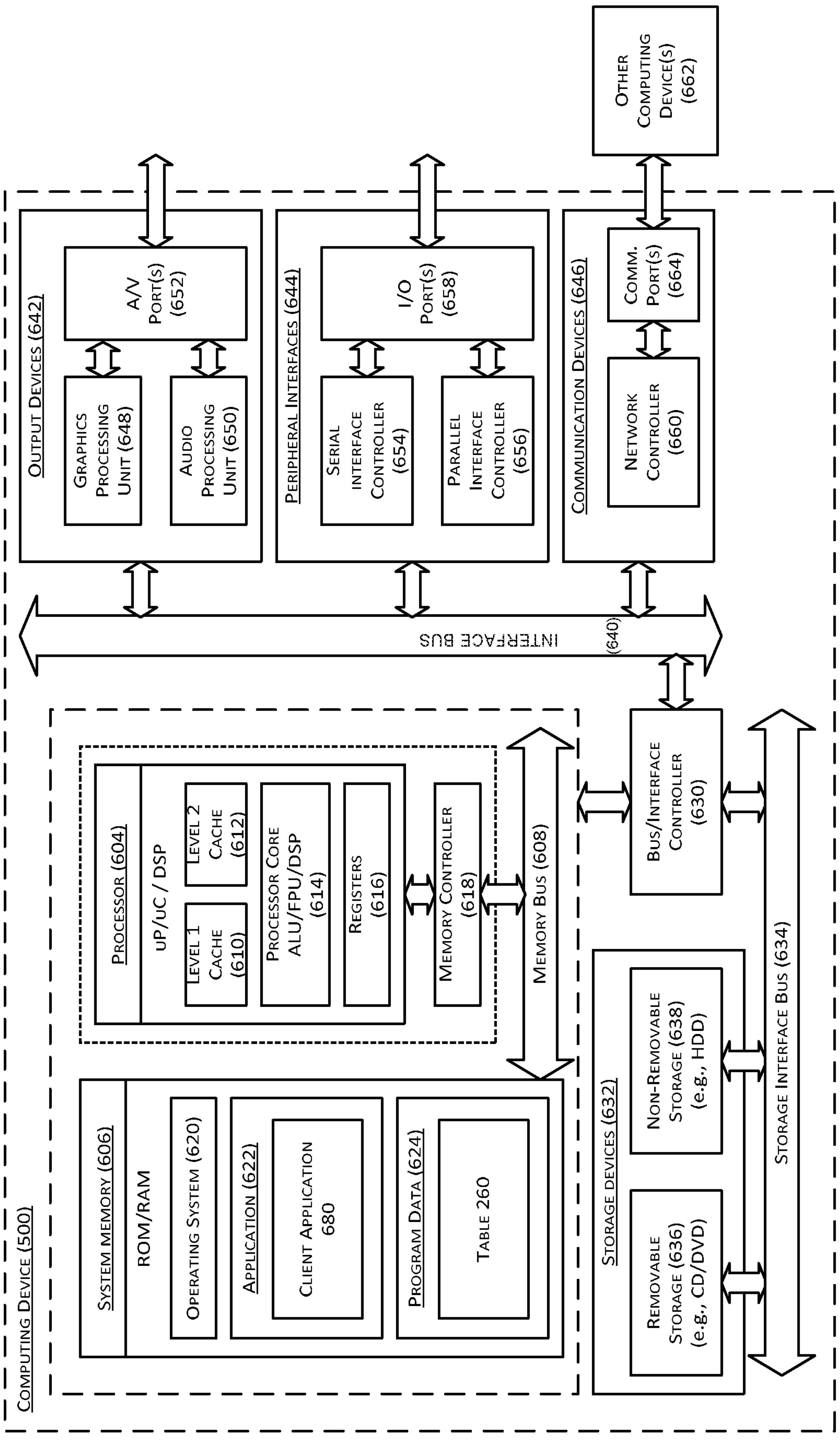
FIG. 6 illustrates a block diagram of a computing device.

FIG. 6 shows sample computing device 600 in which various embodiments of the wearable sensor in a ubiquitous computing environment may be implemented. More particularly, FIG. 6 shows an illustrative computing embodiment, in which any of the operations, processes, etc. described herein may be implemented as computer-readable instructions stored on a computer-readable medium. The computer-readable instructions may, for example, be executed by a processor of a mobile unit, a network element, and/or any other computing device.

In a very basic configuration 602, computing device 600 typically includes one or more processors 604 and a system memory 606. A memory bus 608 may be used for communicating between processor 604 and system memory 606.

Depending on the desired configuration, processor 604 may be of any type including but not limited to a microprocessor (μP), a microcontroller (μC), a digital signal processor (DSP), or any combination thereof. Processor 604 may include one more levels of caching, such as level one cache 610 and level two cache 612, processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624.

Application 622 may include Client Application 680 that is arranged to perform the functions as described herein including those described previously with respect to FIGS. 1-5. Program data 624 may include Table 650, which may alternatively be referred to as "figure table 650" or "distribution table 650," which may be useful for determining patient body temperature as described herein.

Computing device 600 may have additional features or functionality, and additional interfaces to facilitate communications between basic configuration 602 and any required devices and interfaces. For example, bus/interface controller 630 may be used to facilitate communications between basic configuration 602 and one or more data storage devices 632 via storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636, and non-removable storage devices 638 are examples of computer storage media. Computer storage media may include, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include interface bus 640 for facilitating communication from various interface devices, e.g., output devices 642, peripheral interfaces 644, and communication devices 646, to basic configuration 602 via bus/interface controller 630. Example output devices 642 may include graphics processing unit 648 and audio processing unit 650, which may be configured to communicate to various external devices such as a display or speakers via one or more A/V ports 652. Example peripheral interfaces 644 may include serial interface controller 654 or parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 458. An example communication device 646 may include network controller 660, which may be arranged to facilitate communications with one or more other computing devices 662 over a network communication link via one or more communication ports 664.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 may also be implemented as a personal computer including both laptop computer and non-laptop computer configurations.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein may be implemented, e.g., hardware, software, and/or firmware, and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes for determining patient body temperature via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Lastly, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method to determine a patient's core body temperature continuously using a single biometric patch biosensor including a first sensor, a second sensor, and a reusable electronic module, wherein the reusable electronic module includes at least one processor, or a system-on-chip board, and wherein the first sensor and the second sensor are integrated in the single biometric patch biosensor that is attachable to the patient's skin, the method comprising:

measuring, by the first sensor, a first temperature value at a skin surface on a patient body;

measuring, by the second sensor, a second temperature value of ambient air surrounding the first sensor;

passing the first temperature value through an adaptive filter by the electronic module to cancel ambient air temperature fluctuations from the first temperature value at the skin surface and produce an adaptive filter output, wherein the adaptive filter output is subtracted from the second temperature value to produce an error e, and wherein the error e is fed to the adaptive filter to update filter coefficients to minimize the error e;

continuously determining, by the electronic module, a core body thermal exchange at the skin surface on the patient body by subtracting the adaptive filter output from the first temperature value;

continuously determining, by the electronic module, the patient's core body temperature by using the core body thermal exchange;

controlling, by the electronic module, an absolute amplitude level of the core body thermal exchange, wherein the controlling the absolute amplitude level of the core body thermal exchange includes subtracting an AC offset of the core body thermal exchange and adding a DC calibration value that transforms a time varying change of trend of the core body thermal exchange to an absolute scale, and wherein the core body thermal exchange includes at least one of:

in a case of a first calibration, the AC offset is the value of the core body thermal exchange at a temperature sensor settling period, or in a case of a recalibration, the AC offset is the value of the core body thermal exchange at a time of a recalibration request;

outputting, by the electronic module, the patient's core body temperature to a display screen, wherein the patient's core body temperature output is invalidated with a unique numerical code until a settling time flag (ts_flag) and a calibration flag (cal_flag) are onset or changed from 0 to 1; and displaying the patient's core body temperature on the display screen.

2. The method of claim 1, further comprising: initializing the settling time flag (ts_flag) and the calibration flag (cal_flag) with initial values.

3. The method of claim 2, wherein the initial values of the settling time flag and the calibration flag are zero.

4. The method of claim 1, wherein the determining the core body thermal exchange at the skin surface on the patient body by subtracting the adaptive filter output from the first temperature value is according to T_x (n)=f(n)−y(n), wherein the T_x (n) is the core body thermal exchange, wherein the f(n) is the first temperature value, and wherein the y(n) is the adaptive filter output.

5. The method of claim 1, wherein the patient's core body temperature output is the same as that of an input calibration temperature value until the first sensor is determined to have settled down to a steady state or until a desired settling time duration is elapsed.

6. A wireless sensor device for continuous monitoring of a patient's core body temperature comprising a single biometric patch biosensor attachable to the patient's skin, including a reusable electronic module, and a display device, wherein the single biometric patch biosensor also includes an integrated first sensor and second sensor and wherein the reusable electronic module includes at least one processor, or a system-on-chip board, and wherein:

the first sensor is configured to: measure a first temperature value at a skin surface on a patient body;

the second sensor is configured to measure a second temperature value of ambient air surrounding the first sensor;

wherein the electronic module receives the first and second temperature values and implements by the processor an application stored in a memory to:

cancel, by an adaptive filter, ambient air temperature fluctuations from the first temperature value at the skin surface and producing an adaptive filter output, wherein the adaptive filter output is subtracted from the second temperature value to produce an error e, and wherein the error e is fed to the adaptive filter to update filter coefficients to minimize the error e;

continuously determine a core body thermal exchange at the skin surface on the patient body by subtracting the adaptive filter output from the first temperature value, continuously determine a patient's core body temperature by using the core body thermal exchange, control an absolute amplitude level of the core body thermal exchange, wherein the controlling the absolute amplitude level of the core body thermal exchange includes subtracting an AC offset of the core body thermal exchange and adding a DC calibration value that transforms a time varying change of trend of the core body thermal exchange to an absolute scale, and wherein the core body thermal exchange includes at least one of:

in a case of a first calibration, the AC offset is the value of the core body thermal exchange at a temperature sensor settling period, or in a case of a recalibration, the AC offset is the value of the core body thermal exchange at a time of a recalibration request, and output the patient's core body temperature, wherein the patient's core body temperature output is invalidated with a unique numerical code until a settling time flag (ts_flag) and a calibration flag (cal_flag) are onset or changed from 0 to 1; and the display device is configured to display the patient's core body temperature.

7. The wireless sensor device of claim 6, further configured to initialize the settling time flag (ts_flag) and the calibration flag (cal_flag) with initial values.

8. The wireless sensor device of claim 7, wherein the initial values of the settling time flag and the calibration flag are zero.

9. The wireless sensor device of claim 6, wherein the determining the core body thermal exchange at the skin surface on the patient body by subtracting the adaptive filter output from the first temperature value is according to $T\_x(n)=f(n)-y(n)$, wherein the $T\_x(n)$ is the core body thermal exchange, wherein the $f(n)$ is the first temperature value, and wherein the $y(n)$ is the adaptive filter output.

10. The wireless sensor device of claim 6, wherein the patient's core body temperature output is the same as that of an input calibration temperature value until the first sensor is determined to have settled down to a steady state or until a desired settling time duration is elapsed.

11. A non-transitory computer-readable medium storing executable instructions for determining a patient's core body temperature continuously that, in response to execution, cause a processor of a wireless sensor device using a single biometric patch biosensor, including a first sensor, a second sensor, and a reusable electronic module, wherein the reusable electronic module includes at least one processor, or a system-on-chip board, and wherein the first sensor and the second sensor are integrated in the single biometric patch biosensor that is attachable to the patient's skin, to perform operations comprising:

measuring, by the first sensor, a first temperature value at a skin surface on a patient body;

measuring, by the second sensor, a second temperature value of ambient air surrounding the first sensor;

passing the first temperature value through an adaptive filter by the electronic module to cancel ambient air temperature fluctuations from the first temperature value at the skin surface and produce an adaptive filter output, wherein the adaptive filter output is subtracted from the second temperature value to produce an error e, and wherein the error e is fed to the adaptive filter to update filter coefficients to minimize the error e;

continuously determining a core body thermal exchange at the skin surface on the patient body by subtracting the adaptive filter output from the first temperature value;

continuously determining a patient's core body temperature by using the core body thermal exchange;

controlling an absolute amplitude level of the core body thermal exchange, wherein the controlling the absolute amplitude level of the core body thermal exchange includes subtracting an AC offset of the core body thermal exchange and adding a DC calibration value that transforms a time varying change of trend of the core body thermal exchange to an absolute scale, and wherein the core body thermal exchange includes at least one of:

in a case of a first calibration, the AC offset is the value of the core body thermal exchange at a temperature sensor settling period, or in a case of a recalibration, the AC offset is the value of the core body thermal exchange at a time of a recalibration request;

outputting the patient's core body temperature to a display screen, wherein the patient's core body temperature output is invalidated with a unique numerical code until a settling time flag (ts_flag) and a calibration flag (cal_flag) are onset or changed from 0 to 1; and displaying the patient's core body temperature on the display screen.

12. The non-transitory computer-readable medium of claim 11, further comprising instructions to initialize the settling time flag (ts_flag) and the calibration flag (cal_flag) with initial values.

13. The non-transitory computer-readable medium of claim 12, wherein the initial values of the settling time flag and the calibration flag are zero.

14. The non-transitory computer-readable medium of claim 11, wherein the determining the core body thermal exchange at the skin surface on the patient body by subtracting the adaptive filter output from the first temperature value is according to $T\_x(n)=f(n)-y(n)$, wherein the $T\_x(n)$ is the core body thermal exchange,
wherein the $f(n)$ is the first temperature value, and
wherein the $y(n)$ is the adaptive filter output.

15. The non-transitory computer-readable medium of claim 11, wherein the patient's core body temperature output is the same as that of an input calibration temperature value until the first sensor is determined to have settled down to a steady state or until a desired settling time duration is elapsed.

* * * * *